(12) United States Patent
Binder et al.

(10) Patent No.: US 9,884,904 B2
(45) Date of Patent: Feb. 6, 2018

(54) METHOD FOR PURIFYING POLYPEPTIDE SOLUTIONS

(75) Inventors: Vinzenz Binder, Penzberg (DE); Christian Hakemeyer, Munich (DE); Felizitas Schwarz, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 126 days.

(21) Appl. No.: 13/582,606

(22) PCT Filed: Mar. 9, 2011

(86) PCT No.: PCT/EP2011/053547
§ 371 (c)(1),
(2), (4) Date: Sep. 4, 2012

(87) PCT Pub. No.: WO2011/110598
PCT Pub. Date: Sep. 15, 2011

(65) Prior Publication Data
US 2013/0005948 A1    Jan. 3, 2013

(30) Foreign Application Priority Data
Mar. 10, 2010  (EP) .................................... 10156103

(51) Int. Cl.
*A61K 39/395* (2006.01)
*C07K 16/00* (2006.01)
*C07K 1/30* (2006.01)

(52) U.S. Cl.
CPC ............. *C07K 16/00* (2013.01); *C07K 1/30* (2013.01)

(58) Field of Classification Search
None
See application file for complete search history.

(56) References Cited

U.S. PATENT DOCUMENTS

| | | | |
|---|---|---|---|
| 5,196,323 A | | 3/1993 | Bodo et al. |
| 6,140,474 A | * | 10/2000 | Kamada et al. ......... 530/388.85 |
| 2002/0151688 A1 | * | 10/2002 | Ristol Debart et al. ... 530/387.1 |
| 2010/0311952 A1 | | 12/2010 | Falkenstein et al. |
| 2014/0142283 A1 | | 5/2014 | Baehner et al. |
| 2014/0243508 A1 | | 8/2014 | Falkenstein et al. |

FOREIGN PATENT DOCUMENTS

| | | |
|---|---|---|
| CA | 2497364 | 3/2004 |
| EP | 1380589 | 1/2004 |
| EP | 1561756 | 8/2005 |
| WO | 2005/100402 | 10/2005 |
| WO | 2006/099698 | 9/2006 |
| WO | 2008/017963 | 2/2008 |
| WO | 2008/127305 | 10/2008 |
| WO | 2010/040988 | 4/2010 |
| WO | 2011/076683 | 6/2011 |

OTHER PUBLICATIONS

Harris et al., "Protein Purification Methods" A Practical Approach, IRL Press (XP-002516106),:125-175 ( 1989).
Vorlickova et al., Nucl. Acids Res. 27:581-586 ( 1999).
Duhamel et al., Journal of Immunological Methods 31:211-217 ( 1979).
Lydersen et al., Ann. N.Y. Acad. Sci. 745:222-231 ( 1994).
O'Brien et al., J. Acoust. Soc. Am. 52:1251-1255 ( 1972).
International Search Report Written Opinion for PCT/EP2011/053547 dated Jan. 10, 2012 ( Jan. 10, 2012).
Brueggemann et al., J. Exp. Med. 166:1351-1361 ( 1987).
Handbook on Protein Experiments (in Japanese and partial English translation), Yodosha Co., LTD, Apr. 10, 2006, third print, p. 92-96.
The English translation of the Japanese Office Action, dated Mar. 26, 2014, in the corresponding Japanese application No. 2012-556507.
Protein Experimental Methods for Molecular Biology Research (in Japanese and partial English translation), Yodosha Co., LTD, Oct. 30, 1998, p. 84.
Parkinnen et al., 2006, "A modified caprylic acid method for manufacturing immunoglobulin G from human plasma with high yield and efficient virus clearance," Vox Sang. 90(2): 97-104.
Mpandi et al., 2007, "Partitioning and inactivation of viruses by the caprylic acid precipitation followed by a terminal pasteurization in the manufacturing process of horse immunoglobulins," Biologicals, 35(4): 335-41.

* cited by examiner

*Primary Examiner* — Yunsoo Kim
(74) *Attorney, Agent, or Firm* — Jones Day

(57) ABSTRACT

Herein is reported a method for purifying cell cultivation supernatants either directly after fermentation or after one or more preliminary purification steps, such as protein A affinity chromatography. By adjusting the pH value in the acid range and subsequent incubation of the acidified solution host cell nucleic acid and host cell protein can be precipitated but the target polypeptide remains in solution. Thereafter the precipitate and therewith the contaminating host cell components can be removed by a simple physical separation step.

14 Claims, 12 Drawing Sheets

METHOD FOR PURIFYING POLYPEPTIDE SOLUTIONS

RELATED APPLICATIONS

This application is the National Stage of International Application No. PCT/EP2011/053547, filed Mar. 9, 2011, which claims the benefit of European Application No. 10156103.3, filed Mar. 10, 2010, which is hereby incorporated by reference in its entirety.

Herein is reported a method for removing host cell DNA and host cell protein from solutions, such as cell cultivation supernatants or protein A chromatography eluates, without imparting polypeptide content. This is achieved by lowering the pH value of the solution to a value below pH 6 and incubation the solution at this pH value.

BACKGROUND OF THE INVENTION

Biological macromolecules such as recombinant monoclonal antibodies and other proteins are used in a wide array of diagnostic and therapeutic areas. Especially monoclonal antibodies are now widely used in various severe diseases like cancer or rheumatoid arthritis. Commonly, these complex biological molecules are produced by fermentation processes with bacteria, yeasts or mammalian cells. Traditionally, the microbial or mammalian cells are removed from the fermentation broth by centrifugation or filtration and thereafter the cell free supernatant is further purified from fermentation related impurities by various methods like filtration, precipitation and chromatography.

Main impurities from the fermentation processes, beside the media components, are the residual amounts of nucleic acids (host cell DNA (HCDNA) and RNA) and Host Cell Proteins (HCP) from the cells that produce the biological macromolecule. For therapeutic purposes the acceptable concentrations of Host Cell DNA (HCDNA) or Host Cell Protein in the final drug substance are very low in order to reduce adverse effects and guarantee patient safety. Recent improvements in fermentation technology have led to higher cell densities in the production bioreactors, which increase the levels of HCP and HCDNA in the cell free supernatant placing higher demands on the purification process.

Effective and cheap methods to remove large amounts of HCDNA and HCP from cell culture supernatants are therefore highly desirable.

O'Brien, W. D., et al. (J. Acoust. Soc. Am. 52 (1972) 1251-1255) report the ultrasonic investigation of aqueous solutions of deoxyribose nucleic acid. Vorlickova, M., et al. (Nucl. Acids Res. 27 (1999) 581-586) report the dimerization of the guanine-adenine repeat strands of DNA. Acid precipitation of mammalian cell fermentation broth is reported by Lydersen et al. (Lydersen, B. K., et al., Ann. N.Y. Acad. Sci. 745 (1994) 222-231). A method of isolating biomacromolecules using low pH and divalent cations is reported in WO 2008/127305. In EP 1 561 756 and EP 1 380 589 methods for purifying protein are reported.

SUMMARY OF THE INVENTION

Herein is reported a method for purifying a polypeptide from cell cultivation supernatants. It has been found that by adjusting the pH value in the acid range and subsequent incubation of the acidified solution for a specified time host cell nucleic acid and host cell protein precipitate but the target polypeptide remains in solution. Thereafter the precipitate and therewith the contaminating host cell components can be removed by a simple physical separation step. During the treatment of the solution the polypeptide of interest remains in solution whereas host cell contaminants are precipitated.

One aspect as reported herein is a method for producing or obtaining an immunoglobulin comprising the following steps:
  i) adding a solution consisting of an acid and water to a cell cultivation supernatant from which cells and cell debris have been removed for adjusting the pH value to a value of from pH 4.5 to pH 5.5, whereby the solution is essentially free of divalent cations,
  ii) incubating the pH adjusted cell cultivation supernatant, and
  iii) removing the precipitate from the incubated cell cultivation supernatant and thereby producing or obtaining the immunoglobulin,
  wherein the cell cultivation supernatant comprises the immunoglobulin at a concentration of not more than 10 mg/ml,
  wherein the concentration of the added acid is 5.5 mol/l or lower.

In one embodiment at least 90% of the immunoglobulin remains in solution during the incubating step. In a further embodiment at least 95% of the immunoglobulin remains in solution during the incubating step. In also an embodiment more than 98% of the immunoglobulin remains in solution during the incubating step.

In one embodiment the method for producing a polypeptide comprises the following steps:
  a) cultivating a cell comprising a nucleic acid encoding the polypeptide,
  b) removing cells and cell debris from the cell cultivation supernatant,
  c) adjusting the pH value of the cell cultivation supernatant to a value of below pH 5.5,
  d) incubating the pH adjusted cell cultivation supernatant, and
  e) removing the precipitate from the incubated cell cultivation supernatant and thereby producing the polypeptide.

Also an aspect as reported herein is a method for purifying a cell cultivation supernatant comprising the following steps:
  a) adjusting the pH value of the cell cultivation supernatant to a value of below pH 5.5,
  b) incubating the pH adjusted cell cultivation supernatant, and
  c) removing the precipitate from the incubated cell cultivation supernatant and thereby purifying the cell cultivation supernatant.

Another aspect is a method for producing a polypeptide comprising the following steps:
  i) providing a mammalian cell comprising a nucleic acid encoding the polypeptide,
  ii) cultivating the cell under serum free conditions,
  iii) recovering the cell cultivation supernatant, optionally removing cells and cell debris from the cell cultivation supernatant, and
  iv) purifying the cell cultivation supernatant by the following steps and thereby producing a polypeptide:
    a) adding a solution consisting of an acid and water to the cell cultivation supernatant, which solution is essentially free of divalent cations, for adjusting the pH value to a value below pH 5.5,
    b) incubating the pH adjusted cell cultivation supernatant, and c) removing the precipitate from the incubated cell cultivation supernatant, wherein the cell cultivation supernatant comprises the polypeptide at a concentration of not more than 10 mg/ml, wherein the concentration of the added acid is 5.5 mol/l or lower.

In one embodiment adjusting the pH value is to a pH value of from pH 5.5 to pH 3.5. In a further embodiment adjusting the pH value is to a pH value of from pH 5.5 to pH 4.5.

In one embodiment incubating of the pH adjusted cell cultivation supernatant is at a temperature of from 1° C. to 30° C. In another embodiment incubating of the pH adjusted cell cultivation supernatant is at a temperature of from 2° C. to 10° C. In a further embodiment the incubating of the pH adjusted cell cultivation supernatant is at a temperature of about 4° C.

In one embodiment incubating of the pH adjusted cell cultivation supernatant is for about 0.5 hours or more. In another embodiment incubating of the pH adjusted cell cultivation supernatant is for about 0.5 hours to about 72 hours. In a further embodiment incubating of the pH adjusted cell cultivation supernatant is for about 2 hours to about 48 hours. In still another embodiment incubating of the pH adjusted cell cultivation supernatant is for about 20 hours to about 32 hours. In also another embodiment incubating the pH adjusted cell cultivation supernatant is for about 24 hours.

In one embodiment removing cells and cell debris and/or removing of the precipitate is by filtration, settlement, or centrifugation.

In another embodiment the cell cultivation supernatant is a mammalian cell cultivation supernatant.

In one embodiment the polypeptide is an immunoglobulin. In another embodiment the immunoglobulin is an immunoglobulin of the class G. In still another embodiment the immunoglobulin is of the class G subclass IgG1 or subclass IgG4 or variants thereof.

In one embodiment the immunoglobulin is of subclass IgG1 and the incubating is for about 2 hours to about 48 hours at a pH value of from pH 4.5 to pH 3.5.

In one embodiment the immunoglobulin is of subclass IgG4 and the incubating is for about 2 hours to about 30 hours at a pH value of from pH 5.5 to pH 4.5.

DETAILED DESCRIPTION OF THE INVENTION

Herein is reported a method for purifying a polypeptide comprising the following steps:
a) adjusting the pH value of a cell cultivation supernatant comprising the polypeptide to a pH value of from pH 3.5 to 5.5,
b) incubating the pH adjusted cell cultivation supernatant, and
c) removing the precipitate from the incubated cell cultivation supernatant and thereby purifying the polypeptide.

The method as reported herein can be performed directly with the crude cell fermentation supernatant from which cells and cell debris have been removed but also after one or more preliminary purification steps, such as protein A affinity chromatography.

The term "cell cultivation supernatant" denotes a solution that is obtained by the cultivation of a cell secreting a polypeptide of interest. The supernatant comprises beside the secreted polypeptide also components of the employed cell cultivation medium and metabolic components beside the polypeptide of interest secreted by the cells during the cultivation as well as other components of the cultivated cells set free from dead cells during the cultivation or from disintegrated cells during the recovery of the polypeptide from the cells. The cell cultivation supernatant is free of cell debris and/or intact cells. The term also includes a cell cultivation supernatant that has been processed by a single chromatographic purification step, such as protein A affinity chromatography.

The term "polypeptide" denotes a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless. In one embodiment of the method as reported herein is the polypeptide selected from immunoglobulins, immunoglobulin fragments and immunoglobulin conjugates.

The term "immunoglobulin" denotes a protein consisting of two or more polypeptide(s) substantially encoded by immunoglobulin genes. The recognized immunoglobulin genes include the different constant region genes as well as the myriad immunoglobulin variable region genes. An immunoglobulin in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The variable domain of an immunoglobulin's light or heavy chain comprises different segments, i.e. four framework regions (FR) and three hypervariable regions (CDR). The constant region of an immunoglobulin is not involved directly in binding to the immunoglobulin's antigen, but exhibits various effector functions. Depending on the amino acid sequence of the constant region of the heavy chains, immunoglobulins are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the class to which an immunoglobulin belongs the heavy chain constant regions of immunoglobulins are called α (IgA), δ (IgD), ε (IgE), γ (IgG), and μ (IgM), respectively.

The term "immunoglobulin conjugate" denotes a polypeptide comprising at least one domain of an immunoglobulin heavy or light chain conjugated via a peptide bond to a further polypeptide. The further polypeptide is a non-immunoglobulin peptide, such as a hormone, or growth receptor, or cell-toxic peptide, or complement factor, or the like.

In one embodiment the immunoglobulin is an immunoglobulin of the class G. In another embodiment the immunoglobulin is of the class G subclass IgG1 or subclass IgG4 or a variant thereof. The term "variant" denotes a polypeptide that differs in the amino acid sequence from a parent polypeptide's amino acid sequence by virtue of addition, deletion and/or substitution of one or more amino acid residue(s) in the parent polypeptide amino acid sequence. In one embodiment a variant will have an amino acid sequence having at least 90% amino acid sequence identity with the parent polypeptides amino acid sequence, in another embodiment at least 95%, and in a further embodiment at least 99% amino acid sequence identity.

The term "adjusting the pH value" as used herein denotes the addition of an acid to a solution, especially to a cell cultivation supernatant, in order to lower the pH value of the solution to a pH value below pH 7.0. The adjusting can be achieved by the addition of an acidic solution, i.e. of an acid. In one embodiment the adjusting is by the addition of an acidic solution selected from hydrochloric acid, phosphoric acid, acetic acid, and citric acid.

The term "incubating" as used herein denotes that the respective solution is maintained at a set pH value. The incubating can be for a specific time. In one embodiment the incubating is for about 0.5 hours or more. In another embodiment the incubating is for about 0.5 hours to about 72 hours. In a further embodiment the incubating is for about 2 hours to about 48 hours. In still another embodiment the incubating is for about 20 hours to about 32 hours. In also another embodiment the incubating is for about 24 hours. In one embodiment the incubating is for a specific time as defined in the before listed embodiments at a pH value of from pH 3.5 to pH 5.5, especially at a pH value of from pH 4.5 to pH 5.5.

The term "about" as used herein denotes that the directly successive value is no exact value but rather denotes a range. This range is in one embodiment plus or minus 20% of the value, in another embodiment plus or minus 10% of the value and in a further embodiment plus or minus 5% of the value. For example, the term "about 24 hours" denotes the range of from 19.2 hours to 28.8 hours.

The term "essentially free" denotes that to a solution no such compound is added. But the specific compound may be present in minor amounts due to its presence in other compounds comprised in the solution. Generally a solution is essentially free of a compound when this compound is present in the solution at a concentration of 1 mM or less, especially at a concentration of 1 µM or less.

Methods for production of polypeptides are known in the state of the art and comprise protein expression in prokaryotic and eukaryotic cells with subsequent isolation of the polypeptide and usually purification to a pharmaceutically acceptable purity. For example, for the expression of an immunoglobulin in a cell, nucleic acids encoding the respective light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6(R) cells, yeast, or E. coli cells, and the immunoglobulin is recovered from the cells (supernatant or cells after lysis).

The term "cell" as used in the current application denotes any kind of cellular system which can be engineered to produce a polypeptide. In one embodiment the cell is a mammalian cell. In another embodiment the cell is selected from HEK cells and CHO cells.

It has been found that nucleic acid and cell protein of a cultivated cell do precipitate but the secreted polypeptide remains in solution if the pH value of the cell cultivation supernatant is adjusted to a value below pH 5.5 and subsequently the solution is incubated for a specified time at that pH value. Thereafter the precipitate and therewith the contaminating host cell components can be removed by a simple physical separation step.

The method as reported herein can be used for any kind of cell cultivation supernatant, i.e. for eukaryotic cell cultivation supernatant and prokaryotic cell cultivation supernatants. In one embodiment the cell cultivation supernatant is a eukaryotic cell cultivation supernatant. In a further embodiment the supernatant is a mammalian cell cultivation supernatant. In another embodiment the supernatant is a CHO, HEK or Sp2/0 cell cultivation supernatant.

Today almost all cell cultivation processes are performed in the absence of added animal serum. Thus, in one embodiment the cell cultivation supernatant is obtained from a cultivation of the cell under serum free conditions. Additionally with the absence of added animal serum potential interference from compounds not known which are present in the animal serum are excluded and also the concentration of polypeptides in the cell cultivation supernatant is reduced. This is advantageous as generally in methods exploiting precipitation for purification purposes the co-precipitation of the polypeptide of interest can occur and therewith a reduction in yield of the purification process. The same effect can be observed in the presence of the cultivated cell or cell debris therefrom. Therefore, in one embodiment cells and cell debris is removed from the cell cultivation supernatant prior to the adjusting of the pH value.

The concentration of the polypeptide to be purified in the method as reported herein is not more than 10 mg/ml. In one embodiment the concentration of the polypeptide in the cell cultivation supernatant is of from 0.1 mg/ml to about 10 mg/ml. In another embodiment the concentration of the polypeptide in the cell cultivation supernatant is of from 1 mg/ml to 8 mg/ml. In a further embodiment the concentration of the polypeptide in the cell cultivation supernatant is of from 1 mg/ml to 5 mg/ml.

In order to adjust the pH value of the cell cultivation supernatant an acid has to be added to the cell cultivation supernatant. This acid may be any acid as long as that acid does not irreversibly interact with the polypeptide. In one embodiment the acid is selected from hydrochloric acid, phosphoric acid, sulphuric acid, formic acid, acetic acid, propionic acid, malonic acid, succinic acid, adipic acid, lactic acid, and citric acid. It has to be pointed out that the acid when added to the cell cultivation supernatant is an aqueous solution. The solution is consisting of the respective acid as free acid and water and is essentially free of other substances, especially divalent cations. The term "free acid" denotes that the acid is present in a form in which the acidic hydrogen atoms are present and not e.g. exchanged for a different cation. This includes that the form of the acid used to prepare the solution is also the free acid; likewise it is excluded that the acid is used in form of a salt. In one embodiment is the acid selected from hydrochloric acid, phosphoric acid, acetic acid, and citric acid. The concentration of the acid in the respective solution is in one embodiment 5.5 mol/l or less. In another embodiment the concentration of the acid is of from 1 mol/l to 5.5 mol/l. In a further embodiment the concentration of the acid is of from 1.5 mol/l to 4 mol/l. Alternatively the concentration of the acid in the respective solution is in one embodiment 30 wt-% or less. In one embodiment the concentration of the acid is of from 1 wt-% to 30 wt-%. In another embodiment concentration is of from 5 wt-% to 25 wt-%. In a further embodiment is the concentration of the acid of from 10 wt-% to 20 wt-%.

In general if herein ranges of values are given the range does expressly include the boundary points as listed.

After the adjustment of the pH value the pH adjusted cell cultivation supernatant is incubated for a specified time. This specific time is in one embodiment at least about 0.5 hours or more. In another embodiment the specific time is of from about 0.5 hours to about 72 hours. In a further embodiment specific time is of from about 2 hours to about 48 hours. In still another embodiment the specific time is of from about 20 hours to about 32 hours. In also another embodiment the specific time is about 24 hours. In one embodiment incubating the pH adjusted cell cultivation supernatant is at a temperature of from 1° C. to 30° C. In another embodiment incubating the pH adjusted cell cultivation supernatant is at a temperature of from 2° C. to 10° C. In a further embodiment incubating the pH adjusted cell cultivation supernatant is at a temperature of about 4° C.

With a method as reported herein host cell nucleic acid and host cell protein can be precipitated, i.e removed, from a cell culture supernatant without reducing the concentration of the produced polypeptide. An incubation time of about two hours can be sufficient to remove a large amount of host cell nucleic acid. Thus, in one embodiment the incubating is for about two hours. For the precipitation of host cell protein an incubation time of from about two hours to about 48 hours can be sufficient depending on the adjusted pH value and the polypeptide. Thus, in one embodiment the incubating is for about 2 hours at a pH value of about pH 5 at a temperature of about 4° C. In another embodiment the incubating is for about 2 hours to about 48 hours at a pH value of about 5 at a temperature of about 4° C.

In one embodiment the polypeptide is an immunoglobulin.

In one embodiment the immunoglobulin is an immunoglobulin of subclass IgG1. In another embodiment the incubating is for 2 hours to 48 hours at a pH value of from pH 4.5 to pH 3.5 and the immunoglobulin is an immunoglobulin of the subclass IgG1. In a specific embodiment the incubating is for 2 hours to 30 hours.

In one embodiment the immunoglobulin is an immunoglobulin of subclass IgG4. In another embodiment the incubating is for 2 hours to 48 hours at a pH value of from pH 5.5 to pH 4.5 and the immunoglobulin is an immunoglobulin of the subclass IgG4. In a specific embodiment the incubating is at a pH value of about pH 5.

After the incubating the precipitate has to be removed. For the removal any method known to a person of skill in the art can be used. Exemplary methods are filtration, sedimentation and decantation, centrifugation and settlement. In one embodiment the removing of the precipitate is by a method selected from sedimentation, filtration, settlement and centrifugation.

After the removal of the precipitate a further purification of the polypeptide can be performed, e.g. with chromatographic methods known to a person of skill in the art. Therefore in one embodiment the method as reported herein comprises the step of purifying the polypeptide with one or more chromatographic steps.

For the purification of immunoglobulins a combination of different column chromatography steps can be employed. In one embodiment a protein A affinity chromatography is followed by one or two additional chromatographic separation steps, e.g. ion exchange chromatographic steps. Different methods are well established and widespread used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis).

The following examples and figures are provided to aid the understanding of the present invention, the true scope of which is set forth in the appended claims. It is understood that modifications can be made in the procedures set forth without departing from the spirit of the invention.

EXAMPLE 1

Materials and Methods

Antibody

Figure 1:
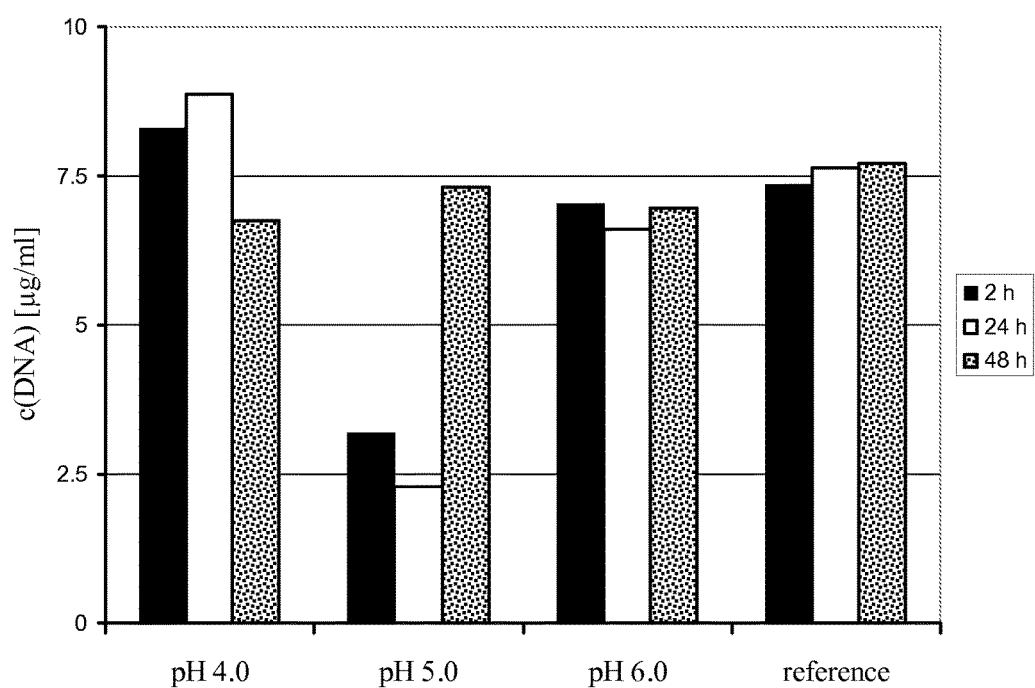
FIG. 1 Host cell DNA content in an anti-EGFR antibody fermentation culture supernatant obtained with a method as reported herein.
Figure 2:
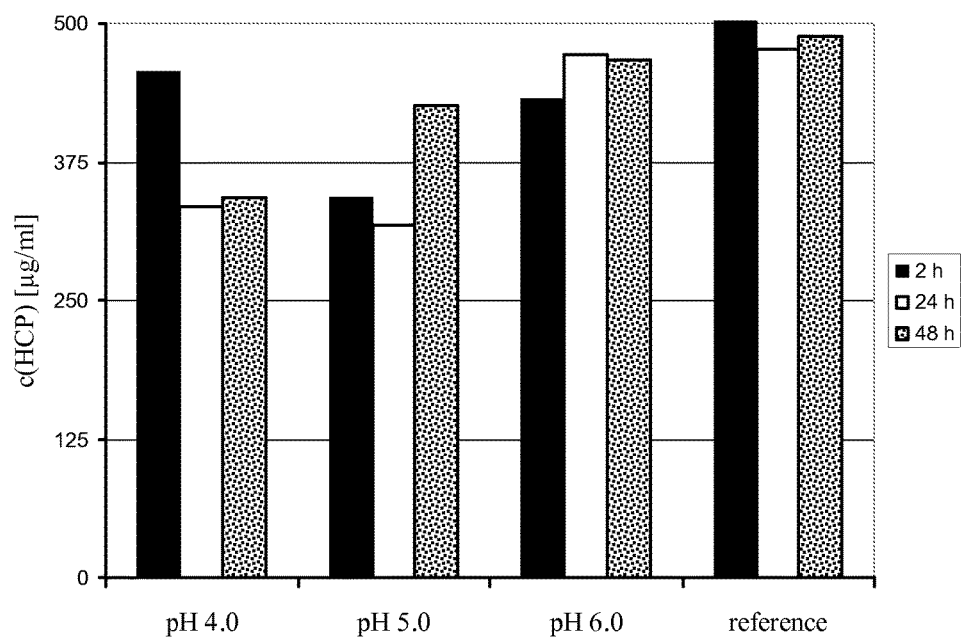
FIG. 2 Host cell protein content in an anti-EGFR antibody fermentation culture supernatant obtained with a method as reported herein.
Figure 3:
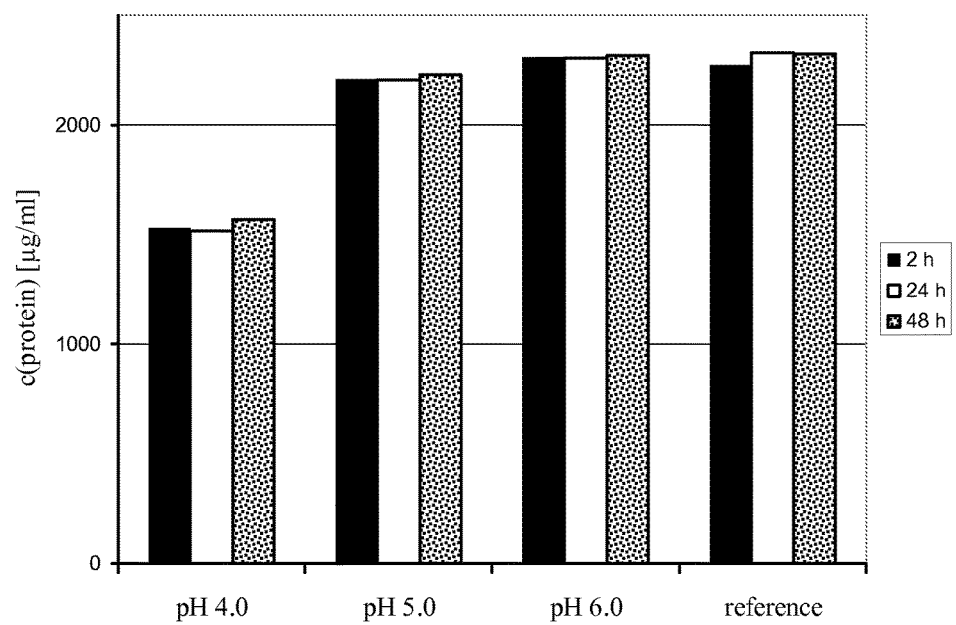
FIG. 3 Antibody content in an anti-EGFR antibody fermentation culture supernatant obtained with a method as reported herein.
Figure 4:
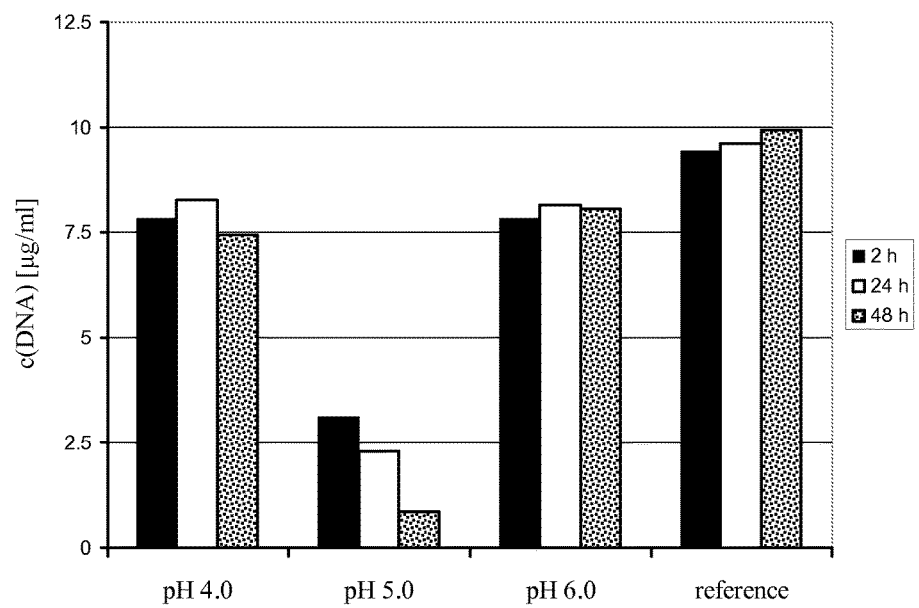
FIG. 4 Host cell DNA content in an anti-PLGF antibody fermentation culture supernatant obtained with a method as reported herein.
Figure 5:
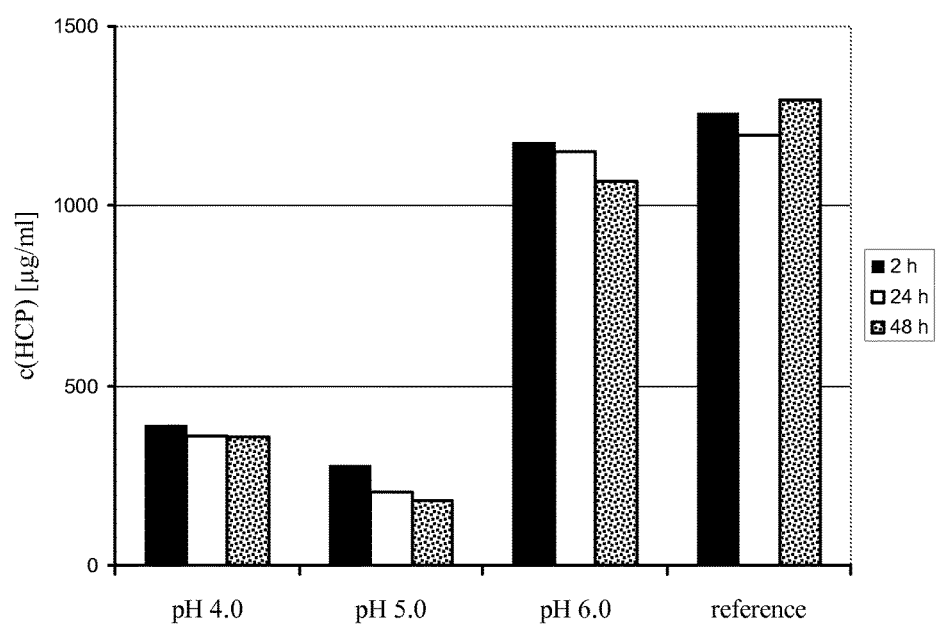
FIG. 5 Host cell protein content in an anti-PLGF antibody fermentation culture supernatant obtained with a method as reported herein.
Figure 6:
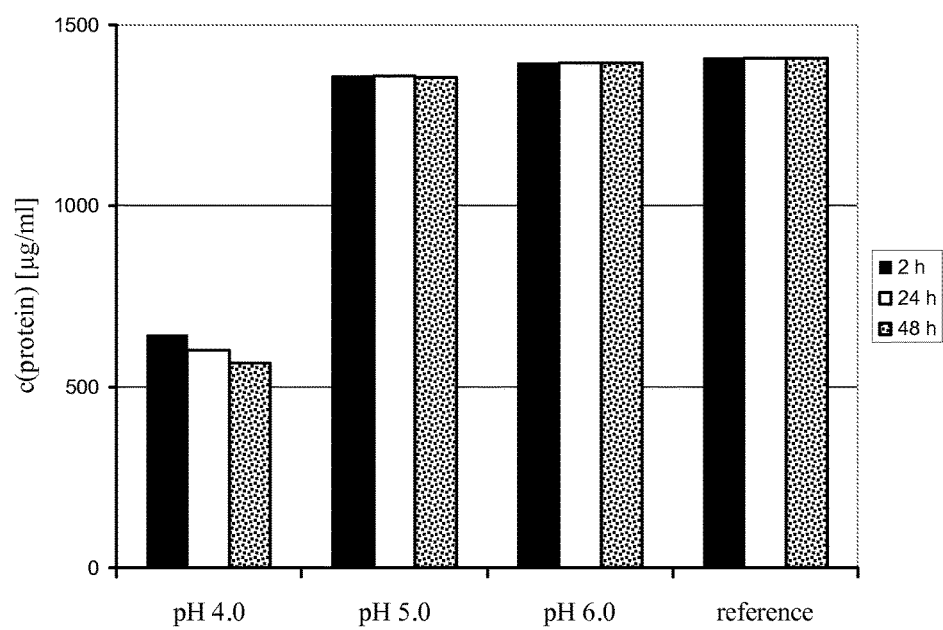
FIG. 6 Antibody content in an anti-PLGF antibody fermentation culture supernatant obtained with a method as reported herein.
Figure 7:
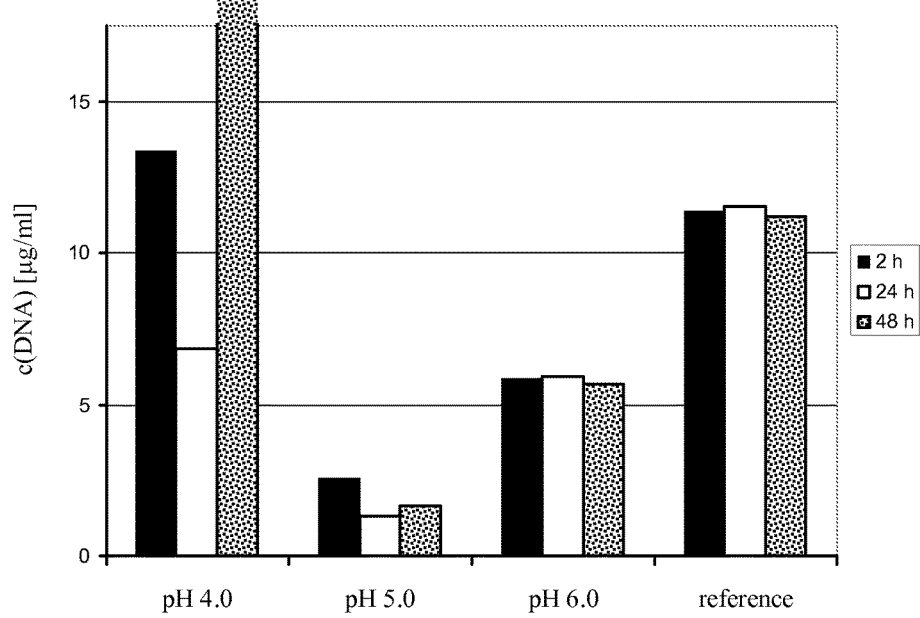
FIG. 7 Host cell DNA content in an anti-P-selectin antibody fermentation culture supernatant obtained with a method as reported herein.
Figure 8:
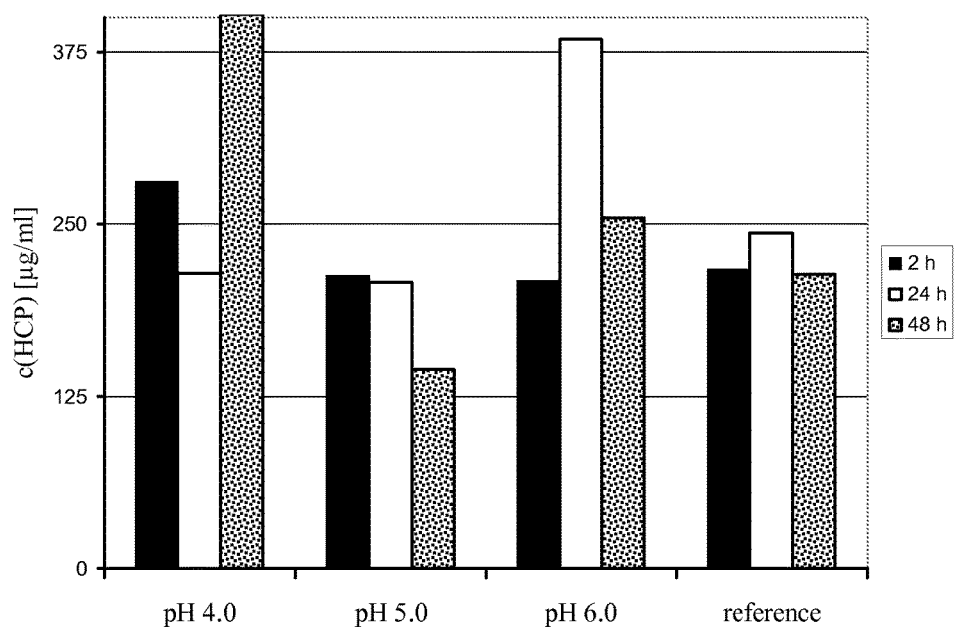
FIG. 8 Host cell protein content in an anti-P-selectin antibody fermentation culture supernatant obtained with a method as reported herein.
Figure 9:
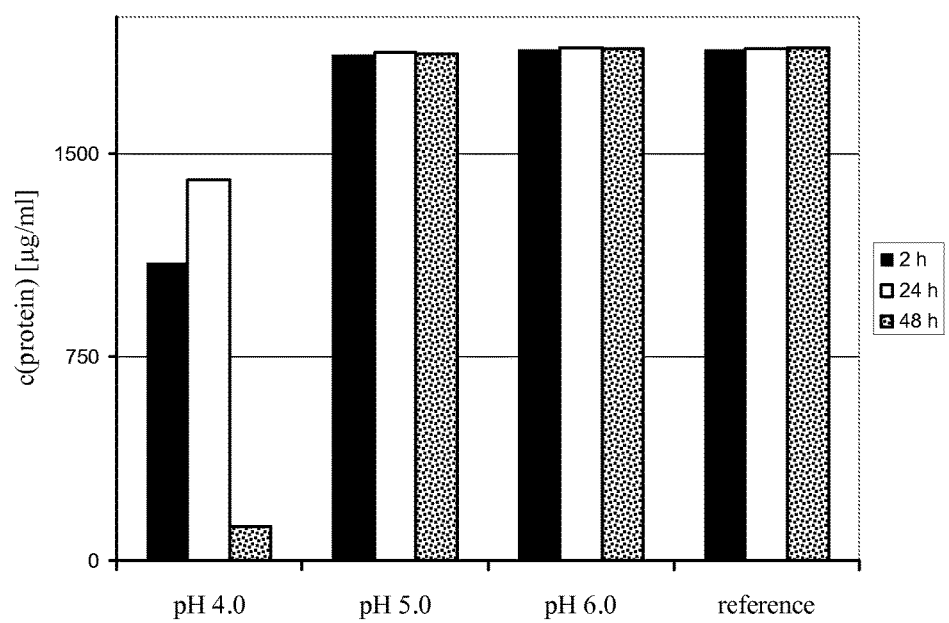
FIG. 9 Antibody content in an anti-P-selectin antibody fermentation culture supernatant obtained with a method as reported herein.
Figure 10:
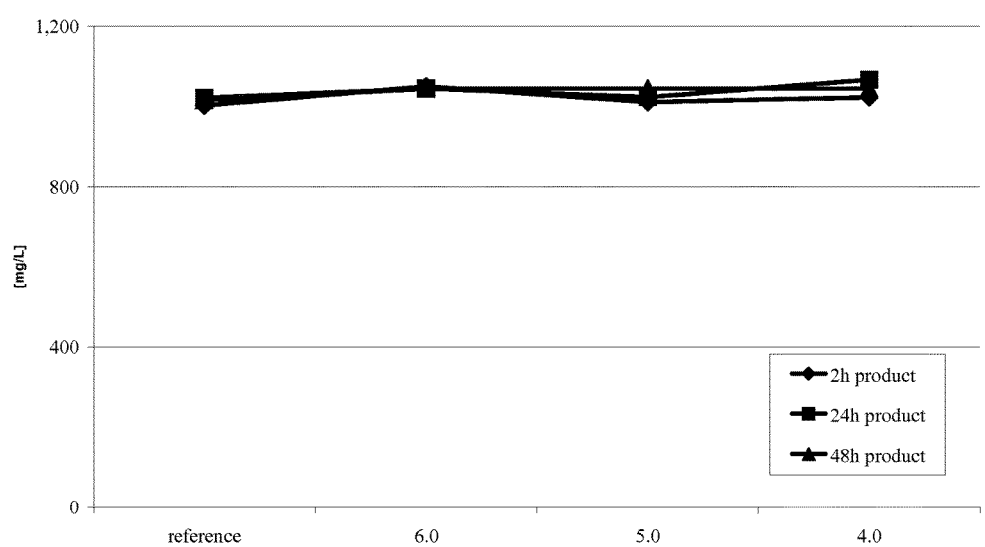
FIG. 10 Antibody content in an anti-PLGF antibody fermentation culture supernatant obtained with a method as reported herein depending on the pH value and the incubation time.
Figure 11:
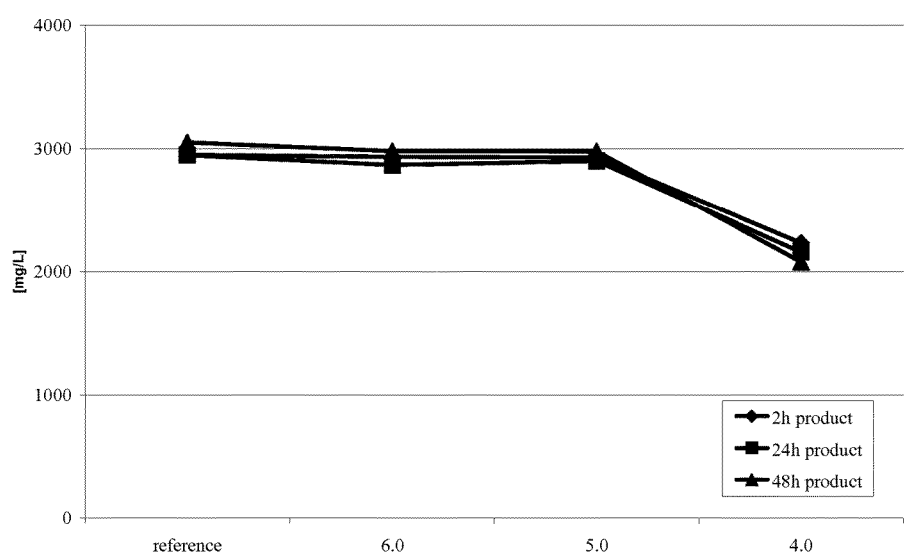
FIG. 11 Antibody content in an anti-P-selectin antibody fermentation culture supernatant obtained with a method as reported herein depending on the pH value and the incubation time.
Figure 12:
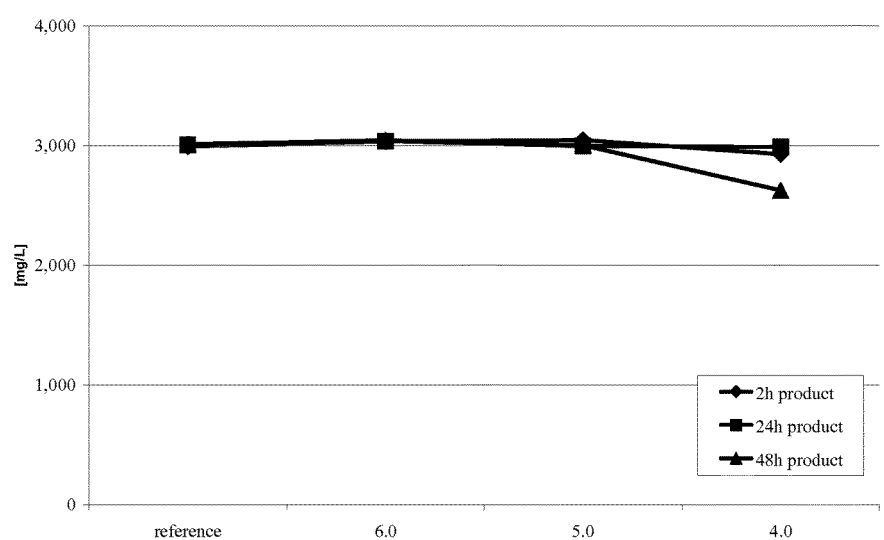
FIG. 12 Antibody content in an anti-HER3 antibody fermentation culture supernatant obtained with a method as reported herein depending on the pH value and the incubation time.

The herein reported method is exemplified with an anti-EGFR antibody as reported in WO 2008/017963.

Another exemplary immunoglobulin is an anti-PLGF antibody as reported in WO 2006/099698.

Another exemplary immunoglobulin is an anti-P-selectin antibody as reported in WO 2005/100402.

Another exemplary immunoglobulin is an anti-HER3 antibody as reported in PCT/EP2010/070062.

DNA

The residual DNA concentration was measured by Q-PCR (quantitative polymerase chain reaction). Therefore, the samples were incubated at high temperatures to denature the DNA in the sample. The DNA was captured from solution by a Silica matrix and eluted therefrom with buffer according to manufacturer's instructions. For the extraction a QIAcube robot was used including the QIAamp Viral RNA Kit (both from Qiagen, Hilden, Germany). Therefore the sample, lysis buffer and carrier RNA were combined and incubated for 10 minutes. Ethanol was added to each tube and the column of the QIAamp Viral RNA Kit was loaded with the sample-ethanol solution and centrifuged. Afterwards a wash solution was applied to the columns and again the column was centrifuged. Thereafter a different wash solution was applied to the column and the column was centrifuged again. After the elution buffer was applied the column is centrifuged twice.

For the quantification of the DNA a LightCycler 2.0 is used (Roche Diagnostics GmbH, Mannheim, Germany). In Table 1 the PCR parameters are outlined.

TABLE 1

PCR parameters.

| cycles | step | analysis mode | temperature | hold time |
|---|---|---|---|---|
| 1 | preincubation | none | 40° C. | 10 min. |
| | | | 95° C. | 10 min. |
| 45 | amplification | quantification | 95° C. | 10 min. |
| | | | 60° C. | 30 sec. |
| | | | 69° C. | 1 sec. |
| 1 | cooling | none | 37° C. | 30 sec. |

During the procedure a DNA strands marked with dye binds to the DNA single strands. During the amplification the fluorescence increases proportional to the quantity of DNA.

HCP

The walls of the wells of a micro titer plate are coated with a mixture of serum albumin and Streptavidin. A goat derived polyclonal antibody against HCP is bound to the walls of the wells of the micro titer plate. After a washing step different wells of the micro titer plate are incubated with a HCP calibration sequence of different concentrations and sample solution. After the incubation not bound sample material is removed by washing with buffer solution. For the detection the wells are incubated with an antibody peroxidase conjugate to detect bound host cell protein. The fixed peroxidase activity is detected by incubation with ABTS and detection at 405 nm.

SEC

The chromatography was conducted with a Tosoh Haas TSK 3000 SWXL column on an ASI-100 HPLC system (Dionex, Idstein, Germany). The elution peaks were monitored at 280 nm by a UV diode array detector (Dionex). After dissolution of the concentrated samples to 1 mg/ml the column was washed with a buffer consisting of 200 mM potassium dihydrogen phosphate and 250 mM potassium chloride pH 7.0 until a stable baseline was achieved. The analyzing runs were performed under isocratic conditions using a flow rate of 0.5 ml/min. over 30 minutes at room temperature. The chromatograms were integrated manually with Chromeleon (Dionex, Idstein, Germany).

IEC

With the Ion Exchange Chromatography the charge heterogeneity of the protein was analyzed. A cation exchange Dionex ProPac chromatography column was used on a Dionex Chromeleon HPLC system.

Protein Determination

A chromatographic method was used to quantify the amount of antibody present in a sample. A Poros A column was used that binds the Fc-region of the antibody. The antibody binds to the column and is subsequently eluted by low pH conditions. Protein concentration was determined by determining the optical density (OD) at 280 nm, with a reference wavelength of 320 nm, using the molar extinction coefficient calculated on the basis of the amino acid sequence.

EXAMPLE 2

Procedure

The samples were obtained directly from the cultivation medium of the respective antibody secreting cell lines. After removal of cells and cell debris the cultivation supernatant was divided into several aliquots of 200 ml each and adjusted to a pH value of pH 4.0, pH 5.0, and pH 6.0, respectively by adding 10% or 20% (v/v) acetic acid. In the reference aliquot the pH value was adjusted if required to approximately pH 7. The aliquots were stored at 4° C. and samples were taken from each aliquot after 2, 24 and 48 hours.

During storage different levels of precipitate formation were observed at the different pH values. The precipitate was removed by sedimentation. Alternatively, the precipitate can be separated by filtration or centrifugation.

After removal of the precipitate the clear liquid phase was analyzed for host cell DNA content, host cell protein (HCP) content and protein amount.

TABLE 2

Host cell DNA content in an anti-EGFR antibody fermentation culture supernatant obtained with a method as reported herein.

| host cell DNA [µg/ml] time [h] | reference | pH 6.0 | pH 5.0 | pH 4.0 |
|---|---|---|---|---|
| 2 | 7.36 | 7.02 | 3.19 | 8.30 |
| 24 | 7.63 | 6.59 | 2.30 | 8.88 |
| 48 | 7.71 | 6.95 | 7.31 | 6.74 |

TABLE 3

Host cell protein content in an anti-EGFR antibody fermentation culture supernatant obtained with a method as reported herein.

| host cell protein [µg/ml] time [h] | reference | pH 6.0 | pH 5.0 | pH 4.0 |
|---|---|---|---|---|
| 2 | 528 | 432 | 343 | 457 |
| 24 | 477 | 471 | 318 | 334 |
| 48 | 489 | 467 | 426 | 343 |

TABLE 4

Antibody content in an anti-EGFR antibody fermentation culture supernatant obtained with a method as reported herein.

| protein [µg/ml] time [h] | reference | pH 6.0 | pH 5.0 | pH 4.0 |
|---|---|---|---|---|
| 2 | 2268 | 2307 | 2207 | 1530 |
| 24 | 2332 | 2305 | 2205 | 1521 |
| 48 | 2321 | 2316 | 2231 | 1572 |

TABLE 5

Host cell DNA content in an anti-PLGF antibody fermentation culture supernatant obtained with a method as reported herein (1st data set).

| host cell DNA [µg/ml] time [h] | reference | pH 6.0 | pH 5.0 | pH 4.0 |
|---|---|---|---|---|
| 2 | 9.45 | 7.81 | 3.11 | 7.81 |
| 24 | 9.61 | 8.16 | 2.30 | 8.26 |
| 48 | 9.93 | 8.07 | 0.84 | 7.44 |

TABLE 5a

Host cell DNA content in an anti-PLGF antibody fermentation culture supernatant obtained with a method as reported herein (2nd data set).

| host cell DNA [µg/g] time [h] | reference | pH 6.0 | pH 5.0 | pH 4.0 |
|---|---|---|---|---|
| 2 | 5543 | 3007 | 286 | 846 |
| 24 | 2750 | 1828 | 65 | 58 |
| 48 | 3484 | 1504 | 103 | 49 |

TABLE 5b

Host cell DNA content in the sediment of an anti-PLGF antibody fermentation culture supernatant obtained with a method as reported herein (2nd data set).

| host cell DNA [µg/g] time [h] | pH 5.0 | pH 4.0 |
|---|---|---|
| 2 | 85395 | 223104 |
| 24 | 183908 | 242948 |
| 48 | 145992 | 229317 |

TABLE 6

Host cell protein content in an anti-PLGF antibody fermentation culture supernatant obtained with a method as reported herein (1st data set).

| host cell protein [µg/ml] time [h] | reference | pH 6.0 | pH 5.0 | pH 4.0 |
|---|---|---|---|---|
| 2 | 1258 | 1176 | 276 | 390 |
| 24 | 1197 | 1151 | 205 | 363 |
| 48 | 1297 | 1069 | 178 | 357 |

TABLE 6a

Host cell protein content in an anti-PLGF antibody fermentation culture supernatant obtained with a method as reported herein (2nd data set).

| host cell protein [mg/g] time [h] | reference | pH 6.0 | pH 5.0 | pH 4.0 |
|---|---|---|---|---|
| 2 | 983 | 1051 | 787 | 292 |
| 24 | 784 | 869 | 501 | 209 |
| 48 | 831 | 874 | 503 | 210 |

TABLE 6b

Host cell protein content in the sediment of an anti-PLGF antibody fermentation culture supernatant obtained with a method as reported herein (2nd data set).

| host cell protein [mg/g] time [h] | pH 5.0 | pH 4.0 |
|---|---|---|
| 2 | 1693 | 1299 |
| 24 | 2236 | 1667 |
| 48 | 2024 | 1021 |

TABLE 7

Antibody content in an anti-PLGF antibody fermentation culture supernatant obtained with a method as reported herein (1st data set).

| protein [µg/ml] time [h] | reference | pH 6.0 | pH 5.0 | pH 4.0 |
|---|---|---|---|---|
| 2 | 1410 | 1393 | 1360 | 644 |
| 24 | 1410 | 1395 | 1358 | 603 |
| 48 | 1410 | 1394 | 1356 | 567 |

TABLE 7a

Antibody content in an anti-PLGF antibody fermentation culture supernatant obtained with a method as reported herein (2nd data set).

| protein [µg/ml] time [h] | reference | pH 6.0 | pH 5.0 | pH 4.0 |
|---|---|---|---|---|
| 2 | 1003 | 1051 | 1012 | 1023 |
| 24 | 1022 | 1045 | 1023 | 1067 |
| 48 | 1016 | 1044 | 1045 | 1045 |

TABLE 8

Host cell DNA content in an anti-P-selectin antibody fermentation culture supernatant obtained with a method as reported herein (1st data set).

| host cell DNA [µg/ml] time [h] | reference | pH 6.0 | pH 5.0 | pH 4.0 |
|---|---|---|---|---|
| 2 | 11.38 | 5.85 | 2.55 | 13.35 |
| 24 | 11.52 | 5.94 | 1.31 | 6.85 |
| 48 | 11.22 | 5.69 | 1.66 | 87.40 |

TABLE 8a

Host cell DNA content in an anti-P-selectin antibody fermentation culture supernatant obtained with a method as reported herein (2nd data set).

| host cell DNA [μg/g] time [h] | reference | pH 6.0 | pH 5.0 | pH 4.0 |
| --- | --- | --- | --- | --- |
| 2 | 22068 | 10228 | 1 | 404 |
| 24 | 18250 | 7953 | 74 | 93 |
| 48 | 19305 | 6280 | 46 | 275 |

TABLE 8b

Host cell DNA content in the sediment of an anti-P-selectin antibody fermentation culture supernatant obtained with a method as reported herein (2nd data set).

| host cell DNA [μg/g] time [h] | reference | pH 6.0 | pH 5.0 | pH 4.0 |
| --- | --- | --- | --- | --- |
| 2 | — | — | 65945 | 79413 |
| 24 | — | — | 90656 | 41701 |
| 48 | 393649 | 139806 | 10126 | 159270 |

TABLE 9

Host cell protein content in an anti-P-selectin antibody fermentation culture supernatant obtained with a method as reported herein (1st data set).

| host cell protein [μg/ml] time [h] | reference | pH 6.0 | pH 5.0 | pH 4.0 |
| --- | --- | --- | --- | --- |
| 2 | 218 | 209 | 212 | 281 |
| 24 | 244 | 384 | 208 | 215 |
| 48 | 214 | 254 | 144 | 1877 |

TABLE 9a

Host cell protein content in an anti-P-selectin antibody fermentation culture supernatant obtained with a method as reported herein (2nd data set).

| host cell protein [mg/g] time [h] | reference | pH 6.0 | pH 5.0 | pH 4.0 |
| --- | --- | --- | --- | --- |
| 2 | 181 | 192 | 120 | 46 |
| 24 | 212 | 199 | 103 | 77 |
| 48 | 202 | 207 | 73 | 77 |

TABLE 9b

Host cell protein content in the sediment of an anti-P-selectin antibody fermentation culture supernatant obtained with a method as reported herein (2nd data set).

| host cell protein [mg/g] time [h] | reference | pH 6.0 | pH 5.0 | pH 4.0 |
| --- | --- | --- | --- | --- |
| 2 | — | — | 290 | 367 |
| 24 | — | — | 693 | 129 |
| 48 | 110 | 108 | 279 | 365 |

TABLE 10

Antibody content in an anti-P-selectin antibody fermentation culture supernatant obtained with a method as reported herein (1st data set).

| protein [μg/ml] time [h] | reference | pH 6.0 | pH 5.0 | pH 4.0 |
| --- | --- | --- | --- | --- |
| 2 | 1880 | 1880 | 1859 | 1094 |
| 24 | 1884 | 1885 | 1867 | 1399 |
| 48 | 1890 | 1881 | 1865 | 127 |

TABLE 10a

Antibody content in an anti-P-selectin antibody fermentation culture supernatant obtained with a method as reported herein (2nd data set).

| protein [μg/ml] time [h] | reference | pH 6.0 | pH 5.0 | pH 4.0 |
| --- | --- | --- | --- | --- |
| 2 | 2950 | 2933 | 2929 | 2231 |
| 24 | 2948 | 2867 | 2900 | 2157 |
| 48 | 3051 | 2981 | 2978 | 2077 |

TABLE 11

Host cell DNA content in an anti-HER3 antibody fermentation culture supernatant obtained with a method as reported herein.

| host cell DNA [μg/g] time [h] | reference | pH 6.0 | pH 5.0 | pH 4.0 |
| --- | --- | --- | --- | --- |
| 2 | 12333 | 15716 | 745 | 65 |
| 24 | 8053 | 19124 | 201 | 14 |
| 48 | 7703 | 15473 | 52 | 13 |

TABLE 11a

Host cell DNA content in the sediment of an anti-HER3 antibody fermentation culture supernatant obtained with a method as reported herein.

| host cell DNA [μg/g] time [h] | reference | pH 6.0 | pH 5.0 | pH 4.0 |
| --- | --- | --- | --- | --- |
| 2 | — | — | 61749 | 57288 |
| 24 | — | — | 67944 | 48404 |
| 48 | 304107 | 186101 | 71909 | 25617 |

TABLE 12

Host cell protein content in an anti-HER3 antibody fermentation culture supernatant obtained with a method as reported herein.

| host cell protein [mg/g] time [h] | reference | pH 6.0 | pH 5.0 | pH 4.0 |
| --- | --- | --- | --- | --- |
| 2 | 522 | 432 | 186 | 40 |
| 24 | 488 | 384 | 141 | 31 |
| 48 | 476 | 346 | 115 | 87 |

TABLE 12a

Host cell protein content in the sediment of an anti-HER3
antibody fermentation culture supernatant obtained
with a method as reported herein.

| host cell protein [mg/g] time [h] | reference | pH 6.0 | pH 5.0 | pH 4.0 |
|---|---|---|---|---|
| 2 | — | — | 770 | 465 |
| 24 | — | — | 612 | 424 |
| 48 | 1167 | 986 | 726 | 275 |

TABLE 13

Antibody content in an anti-HER3 antibody fermentation culture
supernatant obtained with a method as reported herein.

| protein [μg/ml] time [h] | reference | pH 6.0 | pH 5.0 | pH 4.0 |
|---|---|---|---|---|
| 2 | 2992 | 3035 | 3047 | 2928 |
| 24 | 3005 | 3038 | 2997 | 2989 |
| 48 | 3012 | 3044 | 3003 | 2625 |

The invention claimed is:

1. A method for producing an immunoglobulin of the subclass IgG1 or IgG4 comprising the following steps:
   i) adding a solution consisting of an acid and water to a mammalian cell cultivation supernatant from which the mammalian cells and mammalian cell debris have been removed for adjusting the pH value to a value of pH 5, whereby to the solution no divalent cations are added;
   ii) incubating the pH adjusted mammalian cell cultivation supernatant; and
   iii) removing the precipitate from the incubated mammalian cell cultivation supernatant and thereby producing the immunoglobulin;
wherein the mammalian cell cultivation supernatant comprises the immunoglobulin at a concentration of not more than 10 mg/ml, wherein the concentration of the added acid is 5.5 mol/l or lower, and
wherein the incubating is for 2 hours to 48 hours at a pH value of pH 5 and at a temperature of about 4° C.

2. The method according to claim 1, wherein at least 90% of the immunoglobulin remains in solution during the incubating step.

3. The method according to claim 1, wherein at least 95% of the immunoglobulin remains in solution during the incubating step.

4. The method according to claim 1, wherein the incubating is for about 24 hours.

5. The method according to claim 1, wherein the removing is by a method selected from the group consisting of sedimentation, decantation, filtration, settlement, and centrifugation.

6. The method according to claim 1, wherein the acid is selected from the group consisting of acetic acid, citric acid, hydrochloric acid, and phosphoric acid.

7. The method according to claim 1, wherein the concentration of the acid is from 1.5 mol/l to 5.5 mol/l.

8. The method according to claim 1, wherein the acid is acetic acid and the concentration is from 1.5 mol/l to 4 mol/l.

9. The method according to claim 1, wherein the concentration of the acid is from 10 wt-% to 20 wt-%.

10. The method according to claim 1, wherein the concentration of the immunoglobulin is of from 1 mg/ml to 5 mg/ml.

11. The method according to claim 1, wherein the supernatant is a CHO, HEK or Sp2/0 cell cultivation supernatant.

12. The method according to claim 1, wherein the cell is selected from HEK cells and CHO cells.

13. The method according to claim 1, wherein the cell is a CHO cell.

14. The method according to claim 1, wherein the incubating is for about 2 hours at a pH value of about pH 5 and at a temperature of about 4° C.

* * * * *